United States Patent
Blackwell

(12) 
(10) Patent No.: US 6,645,235 B1
(45) Date of Patent: Nov. 11, 2003

(54) HOT/COLD PACK DEVICE

(76) Inventor: Linda R. Blackwell, 1960 N. St., Fairfield, CT (US) 06420

( * ) Notice: Subject to any disclaimer, the term of this patent is extended or adjusted under 35 U.S.C. 154(b) by 56 days.

(21) Appl. No.: 09/978,427

(22) Filed: Oct. 15, 2001

Related U.S. Application Data

(63) Continuation-in-part of application No. 09/684,379, filed on Oct. 6, 2000.

(51) Int. Cl.$^7$ ................................................ A61F 7/00
(52) U.S. Cl. ..................................................... 607/114
(58) Field of Search .......................... 607/96, 108, 109, 607/110, 111, 112, 114; 604/291; D24/206, 207, 208

(56) References Cited

U.S. PATENT DOCUMENTS

| | | |
|---|---|---|
| D37,227 S | 11/1904 | Eggers |
| 1,558,278 A | 10/1925 | Phillips |
| D79,134 S | 8/1929 | Goodwin |
| D81,421 S | 6/1930 | Thayer |
| D111,123 S | 8/1938 | Culverwell |
| D171,466 S | 2/1954 | Schur |
| D238,105 S | 12/1975 | Amend |
| 4,204,110 A | 5/1980 | Smit et al. |
| 4,257,408 A | 3/1981 | Ramey |
| 4,694,829 A | 9/1987 | Frye |
| 4,954,676 A * | 9/1990 | Rankin ........................ 219/200 |
| D342,791 S | 12/1993 | Sparkman |
| 5,584,086 A | 12/1996 | VanWinkle et al. |
| 5,700,284 A | 12/1997 | Owens |
| 5,817,150 A * | 10/1998 | Owens ........................ 607/114 |
| D401,347 S | 11/1998 | Cosentino |
| D405,188 S | 2/1999 | Evans |
| 5,916,088 A * | 6/1999 | Gueli ............................. 5/639 |
| 6,024,762 A * | 2/2000 | Gray ........................... 607/109 |
| 6,168,613 B1 * | 1/2001 | Besse .......................... 607/114 |
| 6,228,108 B1 * | 5/2001 | Lamb et al. ................. 607/112 |

* cited by examiner

*Primary Examiner*—Linda C. M. Dvorak
*Assistant Examiner*—Kenneth Schopfer
(74) *Attorney, Agent, or Firm*—Haugen Law Firm PLLP

(57) ABSTRACT

A hot/cold therapeutic device configured in the shape of an animal, primarily for use by children. The device includes first and second surface portions, wherein the second portion comprises a thermally-conductive material for facilitating efficient heat transfer from within the device.

3 Claims, 2 Drawing Sheets

HOT/COLD PACK DEVICE

CROSS-REFERENCE TO RELATED APPLICATION

The present application is a continuation-in-part of the application Ser. No. 09/684,379, filed Oct. 6, 2000, entitled "HOT/COLD PACK DEVICE", the content of which is incorporated by reference herein.

BACKGROUND OF THE INVENTION

1. Field of the Invention

The present invention relates to therapeutic compresses, and specifically to a therapeutic thermal compress which is configured as a stuffed animal. The device is particularly suited for the therapeutic application of heat or cold to localized areas of the body of a child, as the soft, pliable, child-friendly animal configuration imparts comforting and calming psychological benefits to the user. The configuration includes a body or user contacting thermal transmitting area which is arranged to transmit an elevated (warm) or lowered (cool) temperature from an internally disposed source to the skin zone of the user.

2. Description of the Prior Art and Objectives

In the past, various hot/cold compress devices have been created in novelty configurations such as, for example, stuffed animals. The prior devices typically comprise a therapeutic toy in which an insulation barrier surrounded a thermal container retains a non-toxic solid or particulate material dampened with liquid. See, for example, U.S. Pat. No. 4,694,829. In U.S. Pat. No. 4,204,110 there is disclosed an electric heating appliance in the form of a stuffed animal, doll, or other novelty item.

While the above-noted devices may have been useful and performed reasonably well, the present invention provides the advantages of combining an attractive, soft, plush animal like device with an immediately-usable hot or cold compress with the compress being integral with, or positioned within the plush animal. A portion of the exterior of the device comprises a relatively highly thermally-conductive material, which material may be a thin fabric outer layer. The thermally conductive portion is particularly configured to facilitate an immediate and more rapid transfer of heat or cold from the compress to the child's body.

A primary objective of the present invention is to provide a device in the form or configuration of a stuffed or plush animal toy, but having an area or zone adapted for the expedited transfer of heat or cold to an adjacent human body-part for therapeutic purposes.

Another object of the invention is the provision of a therapeutic heating or cooling device comprising an stuffed or plush animal shape, the preferred toy shape being that of a seal, penguin, or polar bear.

Yet another object of the invention is the provision of a therapeutic compress device which is of selected shape and texture to be of soothing comfort to children.

Still another object of the invention is to help maintain and/or sustain the attention of the child so that the compress device will more likely be held in place on the affected body part for the required amount of time so that optimal therapeutic benefit may be realized.

Another object of the invention is to provide physiological therapy with comforting and calming psychological benefits.

Other objects and novel features, and further scope of applicability of the present invention will be set forth in part in the detailed description and drawings, and will become apparent to those skilled in the art upon examination of the following. The objects and advantages of the present invention may be realized as particularly pointed out in the appended claims.

SUMMARY OF THE INVENTION

The present invention comprises a therapeutic compress configured in the shape of an animal figure, namely a seal, polar bear, or penguin. A portion of the outer layer consists of a washable plush acrylic fabric possessing insulative properties. The outer layer may be integral with a gel pack hot or cold compress disposed therewithin. An external surface of the compress preferably forms a portion of the outer layer, and in turn functions as the thermally conductive interface between the heated or cooled gel pack and the skin of the human user, facilitating an immediate and expedited transfer of the soothing heat or cold.

BRIEF DESCRIPTION OF THE DRAWINGS

For a more thorough understanding of the invention reference is now made to the following detailed description and drawings in which.

DETAILED DESCRIPTION OF THE PREFERRED EMBODIMENT

Figure 1:
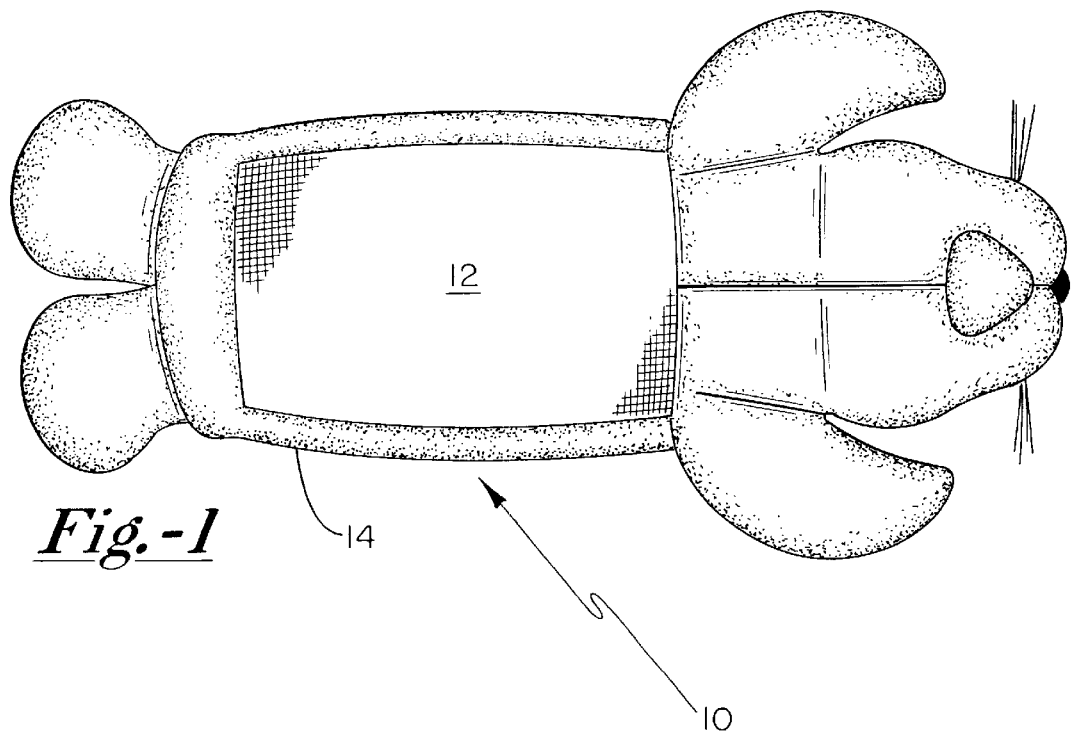
FIG. 1 is a bottom plan view of the hot/cold pack device in the configuration of a toy seal, showing the thermal interface portion.
Figure 2:
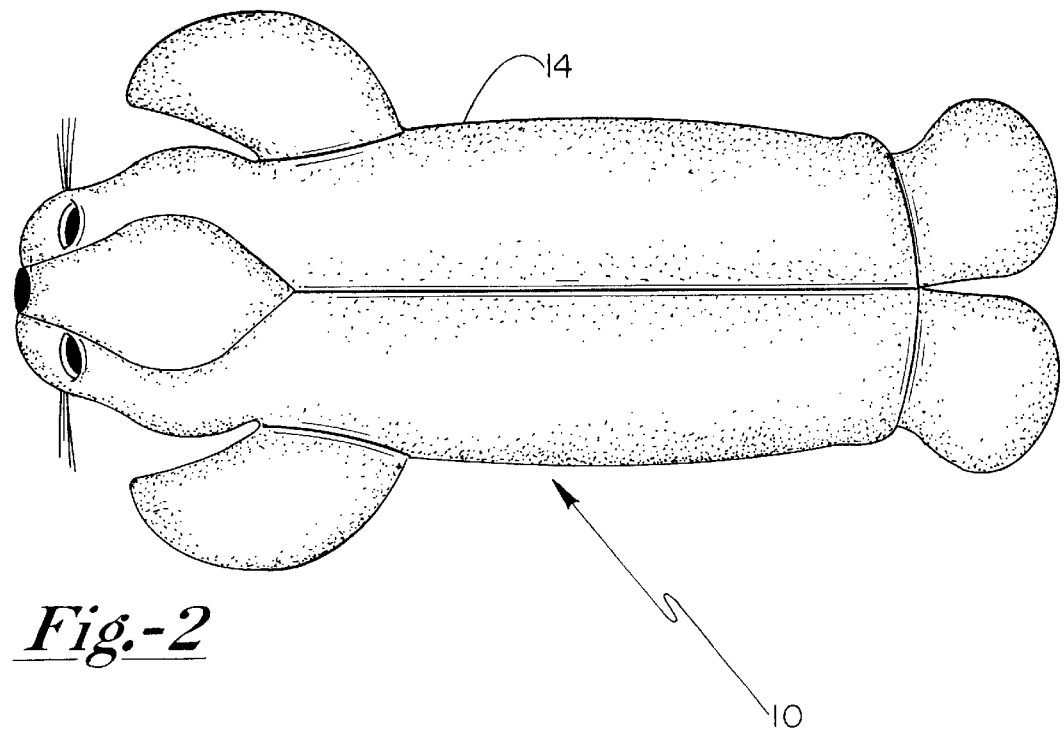
FIG. 2 is a top plan view of the hot/cold pack device in the configuration of a toy seal.

Referring to FIGS. 1 and 2, the device generally designated 10 is a hot/cold pack device in the form or configuration of an animal, such as a seal as seen in the present embodiment. A first portion of the outer covering as seen at element 14 is constructed of a plush acrylic fabric, which has thermally insulative properties. A second portion of the outer covering is in the form of a thin layer of material 12, preferably in the shape of a square or rectangle. Other configurations, such as oval or circular may also be used. Material 12 comprises a thermally-conductive interface between the cooling or heating substance within device 10 and the skin of the human user. The thermally-conductive properties attributable to the material 12 allow an efficient transfer of heat, so that the soothing benefits of the compress may be more immediately realized.

In some embodiments of the present invention, material 12 may comprise an external boundary layer containing a thermal-retention substance therewithin, which thermal-retention substance provides the hot and cold temperature functionality of device 10. Preferably, such material 12 is integral with outer fabric layer 14, such that thermally-conductive material 12 forms a portion of the outer covering of device 10. Through such an embodiment, device 10 itself may be pre-heated or pre-cooled to attain desired therapeutic temperatures in the thermal-retention substance stored therewithin. In such a manner, handling of a separate heat-sink device is not required. Material 12 preferably comprises a woven material, such as nylon or polyester, but may also be formed of any relatively thermally-conductive material for efficiently transferring heat from within device 10 to the skin of the user.

Figure 3:
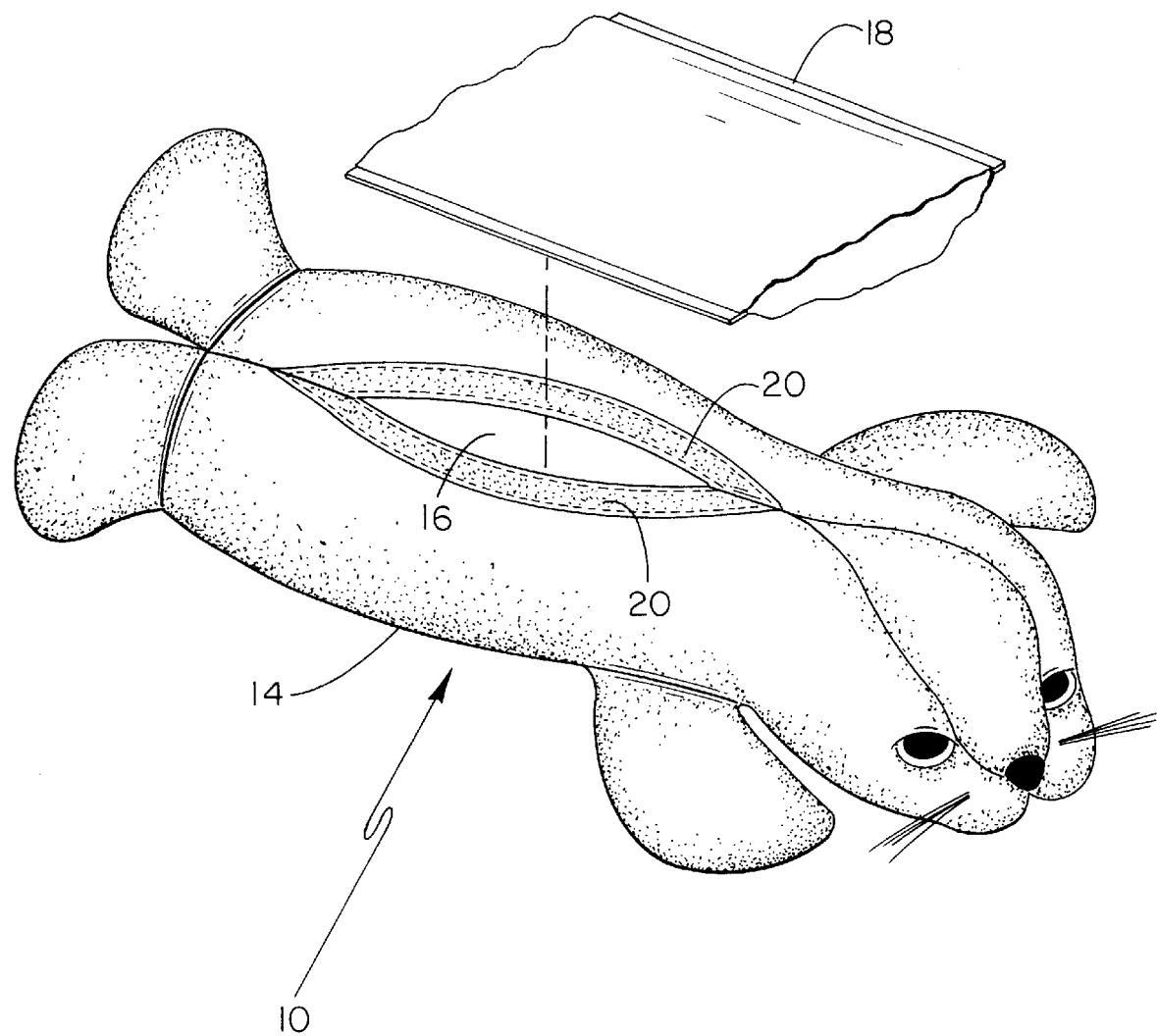
FIG. 3 is a side elevational view of an alternative embodiment of the present invention, including a cavity or container pocket wherein a distinct gel pack body is positioned within a cavity of the outer body.

As shown in FIG. 3, an alternative embodiment of the device 10 is positioned for placement of the gel pack 18 into the interior cavity or container receiving pocket 16. Hook and loop strip members 20 are attached to outer element 14 preferably at a location other than on the interface material 12 to facilitate releasable closing of the opening so that the gel pack 18 may be changed as required so that heating or cooling properties of the device may be maintained. Other fastener may suitably be employed.

The above has been given only by way of illustrative example for the present invention and all such modifications and variations that would be apparent to persons skilled in the art are deemed to fall within the broad scope of this invention as defined in the claims.

What is claimed is:

1. A toy therapeutic device comprising:

an outer surface forming a figure body for enclosing a thermal-retention substance therewithin, said surface including first and second portions disposed in integral relationship with one another, said first portion being a relatively soft and thermally-insulative fabric material, and said second portion being a relatively thermally-conductive material for facilitating efficient heat transfer from the thermal-retention substance disposed within said body to the skin surface of a user, said first and second portions being mutually exclusive of one another, in that said second portion includes only the relatively thermally conductive material, said thermal-retention substance being positionably retained immediately adjacent to said second portion of said outer surface for direct thermal transfer therethrough.

2. A toy therapeutic device as in claim 1 which is configured in the form of a stuffed animal.

3. A toy therapeutic device as in claim 1 wherein said second portion comprises nylon.

* * * * *